United States Patent [19]
Karim et al.

[11] Patent Number: 6,013,597
[45] Date of Patent: Jan. 11, 2000

[54] CATALYSTS FOR THE OXIDATION OF ETHANE TO ACETIC ACID PROCESSES OF MAKING SAME AND, PROCESSES OF USING SAME

[75] Inventors: Khalid Karim, Manchester, United Kingdom; Mohammed H. Al-Hazmi, Riyadh, Saudi Arabia; Edouard Mamedov, Baku, Azerbaijan

[73] Assignee: Saudi Basic Industries Corporation, Saudi Arabia

[21] Appl. No.: 08/932,075

[22] Filed: Sep. 17, 1997

[51] Int. Cl.$^7$ .............. B01J 27/198; B01J 27/19
[52] U.S. Cl. ............ 502/209; 502/206; 502/211; 502/215; 502/308; 502/311; 502/321; 502/349; 502/353; 502/312
[58] Field of Search .............. 502/206, 209, 502/211, 215, 308, 311, 321, 349, 353, 312

[56] References Cited

U.S. PATENT DOCUMENTS

| | | | |
|---|---|---|---|
| 3,057,915 | 10/1962 | Riemenschneider et al. | 260/533 |
| 3,240,805 | 3/1966 | Naglieri | 260/533 |
| 3,301,905 | 1/1967 | Riemenschneider et al. | 260/597 |
| 4,148,757 | 4/1979 | Brazdil et al. | 252/432 |
| 4,250,346 | 2/1981 | Young et al. | 585/658 |
| 4,339,355 | 7/1982 | Decker et al. | 252/464 |
| 4,524,236 | 6/1985 | McCain | 585/658 |
| 4,568,790 | 2/1986 | McCain | 585/658 |
| 4,596,787 | 6/1986 | Manyik et al. | 502/312 |
| 4,899,003 | 2/1990 | Manyik et al. | 585/313 |
| 5,049,692 | 9/1991 | Hatano et al. | 558/319 |
| 5,162,578 | 11/1992 | McCain, Jr. et al. | 562/512.2 |
| 5,198,580 | 3/1993 | Bartek et al. | 562/542 |
| 5,300,682 | 4/1994 | Blum et al. | 562/512.2 |

FOREIGN PATENT DOCUMENTS

| | | |
|---|---|---|
| 0 518 548 | 12/1962 | European Pat. Off. . |
| 0 294 845 | 12/1988 | European Pat. Off. . |
| 0 407 091 | 1/1991 | European Pat. Off. . |
| 0 480 594 | 4/1992 | European Pat. Off. . |
| 0 620 205 | 10/1994 | European Pat. Off. . |
| 0 627 401 | 12/1994 | European Pat. Off. . |

OTHER PUBLICATIONS

E.M. Thorsteinson et al. "The Oxidative Dehydrogenetion of Ethane ..." *Journal of Catalysis* vol. 52, pp. 116–132 (1978).

*Primary Examiner*—Rosalynd Keys
*Attorney, Agent, or Firm*—Whitman Breed Abbott & Morgan LLP

[57] ABSTRACT

An oxide catalyst comprising the elements Mo, V and Nb with small amounts of phosphorus, boron, hafnium, Te and/or As. The modified catalyst provides both higher selectivity and yield of acetic acid in the low temperature oxidation of ethane with molecular oxygen-containing gas. A process for the higher selective production of acetic acid by the catalytic oxidation of ethane with oxygen, in the presence of the improved catalyst.

35 Claims, 2 Drawing Sheets

CATALYSTS FOR THE OXIDATION OF ETHANE TO ACETIC ACID PROCESSES OF MAKING SAME AND, PROCESSES OF USING SAME

BACKGROUND OF THE INVENTION

1. Field of the Invention

The invention relates to improved catalysts, methods of making the same and to processes of using the same for low temperature oxydehydrogenation of ethane to acetic acid and ethylene providing increased ethane conversion and higher selectivity to acetic acid.

2. Description of the Related Art

Documents are cited in this disclosure with a full citation for each appearing thereat. These documents pertain to the field of this invention; and, each document cited herein is hereby incorporated by reference.

The use of molybdenum and vanadium containing catalyst systems for low temperature oxydehydrogenation of elthane to ethylene has become known since the publication of "The Oxidative Dehydrogenation of Ethane over Catalyst Containing Mixed Oxide of Molybdenum and Vanadium" by E. M. Thorsteinson, T. P. Wilson, F. G. Young and P. H. Kasai, *Journal of Catalysis*, vol. 52, pp. 116–132 (1978). This paper discloses mixed oxide catalysts containing molybdenum and vanadium together with another transition metal oxide, such as Ti, Cr, Mn, Fe, Co, Ni, Nb, Ta, or Ce. The disclosed catalysts are active at temperatures as low as 200° C. for the oxydehydrogenation of ethane to ethylene. Some acetic acid is produced as a by-product by these methods.

Several U.S. Pat. Nos. (4,250,346, 4,524,236, 4,568,790, 4,596,787 and 4,899,003) disclose low temperature oxydehydrogenation of ethane to ethylene. U.S. Pat. No. 4,250,346 discloses the use of catalysts of the formula $Mo_hV_iNb_jA_k$ in which A is Ce, K, P, Ni, and/or U, h is 16, i is 1 to 8, j is 0.2 to 10, and k is 0.1 to 5. The patent discloses one phosphorus-containing catalyst which is set forth in the examples having a $Mo_{16}V_4Nb_4P_4$ oxide composition supported by silica-alumina. This catalyst is inactive in the oxidation of ethane at 320° C. Furthermore, this patent reference is concerned with obtaining a high selectivity to ethylene, rather than acetic acid.

U.S. Pat. No. 4,454,326 is directed to the use of a calcined catalyst of the formula $Mo_aV_bNb_cSb_dX_e$.

The above cited patents reference other patents concerned with the production of ethylene from ethane by the oxydehydrogenation process wherein acetic acid is formed as a by-product.

European Pat. Publication EP 02 94 845 discloses a process for the higher selective production of acetic acid by the oxidation of ethane with oxygen in contact with a mixture of catalysts consisting of (A) a catalyst for oxydehydrogenation of ethane to ethylene and (B) a catalyst for hydration/oxidation of ethylene. The ethane oxydehydrogenation catalyst is represented by the formula $Mo_xV_yZ_z$, wherein Z can be nothing or Nb, Sb, Ta, W and many other metals.

European Patent Publication EP 04 80 594 is directed to the use of an oxide catalyst composition comprising tungsten, vanadium, rhenium and at least one of the alkaline metals for the production of ethylene and acetic acid by oxidation of ethane with a molecular oxygen containing gas. The replacement of tungsten in whole or part by molybdenum carried out in EP 04 07 091 results in an increase in selectivity to acetic acid at the expense of the selectivity to ethylene.

EP 05 18 548 relates to a process for making acetic acid by oxidation of ethane in contact with a solid catalyst having empirical formula $VP_aM_bO_x$, where M is one or more optional elements selected from Co, Cu, Re, Nb, W and many other elements, excluding molybdenum, a is 0.5 to 3, b is 0 to 0.1. The patent publication discloses that the catalyst contains a crystalline vanadyl pyrophosphate phase.

European Patent Publication EP 06 27 401 describes the use of a $V_aTi_bO_x$ catalyst for oxidation of ethane to acetic acid. The catalyst composition may comprise additional components from a large list of possible elements.

It would be desirable to produce an improved catalyst for use in the oxidation of ethane to acetic acid with higher yields and increased selectivity of acetic acid.

SUMMARY OF THE INVENTION

According to the present invention, an improved MoVNb catalyst useful for the conversion of ethane to acetic acid is provided. Using the improved catalyst, ethane is oxidized with molecular oxygen to acetic acid in a gas phase reaction at relatively high levels of conversion, selectivity and productivity and at temperatures 150° C. to 450° C. and at pressures 1–50 bar. The modified MoVNb catalytic system provide yield of acetic acid up to 40% as compared to the unmodified catalyst. The improved catalyst is formed from a calcined composition of $Mo_aV_bNb_cX_d$ wherein:

X is at least one promoter element selected from the group consisting of: P, B, Hf, Te, and As;
a is about 1 to 5;
b is 1;
c is about 0.01 to 0.5;
d is about 0 to 0.1.

The numerical values of a, b, c and d represent the relative gram-atom ratios of the elements Mo, V, Nb and X, respectively, in the catalyst. The elements are present in combination with oxygen in the form of various oxides. The catalysts are preferably produced using the methods disclosed herein.

BRIEF DESCRIPTION OF THE DRAWINGS

Specific embodiments of the present invention will now be described further, by way of example, with reference to the accompanying drawings, in which.

DESCRIPTION OF THE PREFERRED EMBODIMENTS

Figure 1:
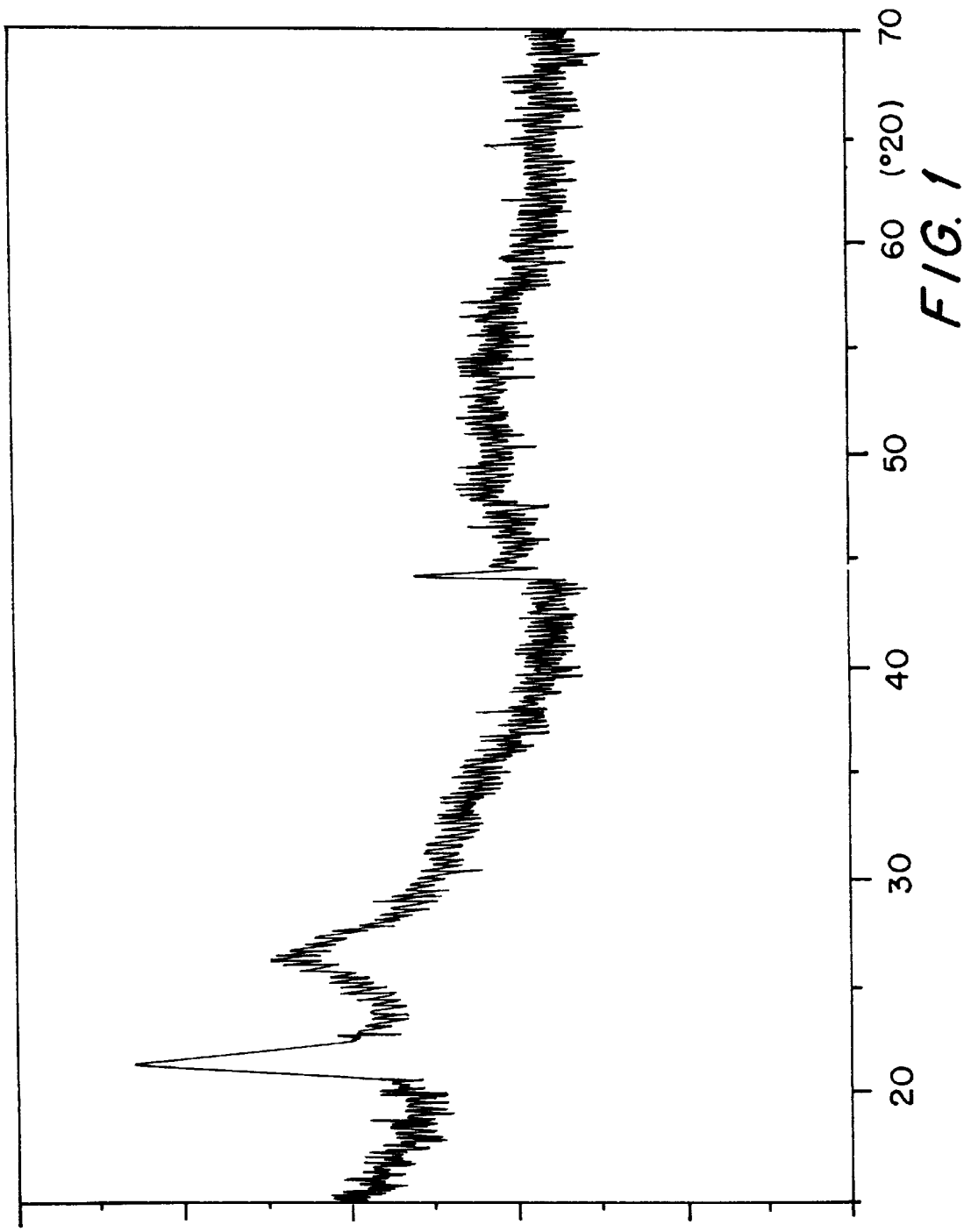
FIG. 1 is an XRD pattern for a catalyst modified with promoter P according to one embodiment of the invention.

One aspect of the invention relates to a catalyst for selective oxidation of ethane to acetic acid containing a catalyst composition comprising the elements Mo, v, Nb and X, in the form of oxides, in the following ratio:

$$Mo_A V_B Nb_C X_D$$

wherein X is at least one promoter element selected from the group consisting of P, B, Hf, Te, and As;
A is a number ranging from about 1 to about 5;
B is 1;
C is a number ranging from about 0.01 to about 0.5; and
D is a number ranging from greater than 0 to about 0.1.

Another aspect of the invention relates to a catalyst for selective oxidation of ethane to acetic acid containing a catalyst composition comprising the elements Mo, V, Nb and X and oxygen in the following ratio:

$$Mo_A V_B Nb_C X_D O_Y$$

wherein X is at least one promoter element selected from the group consisting of P, B, Hf, Te, and As;
A is a number ranging from about 1 to about 5;
B is 1;
C is a number ranging of from about 0.1 to about 0.5;
D is a number ranging of from greater than 0 to about 0.1; and
Y is 5.25 to 20 and is a number determined by the valence requirements of the other elements in the catalyst composition.

A still further aspect of the invention relates to a catalyst for selective oxidation of ethane to acetic acid made by process comprising the steps of:

(a) combining the elements Mo, V, Nb and X in the following ratio:

$$Mo_A V_B Nb_C X_{DY}$$

to form a mixture,
wherein X is at least one promoter element selected from the group consisting of P, B, Hf, Te, and As;
A is a number ranging from about 1 to about 5;
B is about 1;
C is a number ranging of from about 0.01 to about 0.5; and
D is a number ranging from greater than 0 to about 0.1; and (b) calcining the mixture to form the catalyst.

According to one embodiment of the invention, X comprises P, A ranges from about 2 to about 3, C ranges from about 0.20 to about 0.45 and D ranges from about 0.01 to 0.1. According to another embodiment of the invention, X comprises P, A is about 2.5, C is about 0.3 and D is about 0.01 to 0.1. According to yet another embodiment of the invention, X comprises P, A is 2.5, C is 0.32 and D is about 0.03 to about 0.05. Preferably, D is about 0.04.

The prior art has not disclosed or suggested the advantages of the catalysts disclosed in present invention provided by adding only small amounts of phosphorus, B, Hf, Te, and/or As to catalysts for oxidation of ethane to acetic acid. It is well known that catalyst performance, as a function of the amount of dopant, frequently passes through a maximum. This is observed in the present invention as well (see Table 3). As can be seen from the Examples 1–6 described below, MoVNb oxide catalysts modified with small amounts of phosphorus displayed considerably higher selectivity to acetic acid than the unmodified catalyst. The same catalyst modified with larger amounts of phosphorus in Examples 7 and 8 showed lower selectivity to acetic acid as compared to the unmodified catalyst used in Example 1. And finally, the catalyst used in Example 9 contained the amount of phosphorus commensurable with the amounts of basic elements. This sample did not show any activity in the oxidation of ethane in agreement with Example 48 of the U.S. Pat. No. 4,250,346. Similar results for boron (example 11) and tellurium (example 10) modified catalysts, having a higher selectivity to acetic acid as compared to unmodified (example 1) are obtained.

The catalyst of the invention can be formed with or without a support. Suitable supports for the catalyst include alumina, silica, titania, zirconia, zeolites, molecular sieves and other micro/nanoporous materials, and mixtures thereof. When used on a support, the supported catalyst usually comprises from about 10 to 50% by weight of the catalyst composition, with the remainder being the support material.

A still further aspect of the invention relates to a process of forming the inventive catalyst comprising the steps of:

(a) forming a mixture containing Mo, V, Nb and X in a solution;
(b) drying the mixture to form a dried solid material; and
(c) calcining the dried solid material to form the catalyst.

The selection of the compounds used as well as the specific procedures followed in preparing a catalyst can have a significant effect on the performance of a catalyst. The elements of the catalyst's resultant composition are preferably in combination with oxygen as oxides.

The catalyst according to the invention may be prepared from a solution of soluble compounds (salts, complexes or other compounds) of each of the metals. The solution is preferably an aqueous system having a pH of 1 to 10, more preferably at a pH of 1 to 7, and at a temperature of from about 30° C. to about 100° C.

According to one preferred embodiment, a mixture of compounds containing the elements is prepared by dissolving sufficient quantities of soluble compounds and dispersing the insoluble compounds so as to provide the desired gram-atom ratios of the elements in the catalyst composition. The catalyst composition is then prepared by removing the water or/and other solvent from the mixture of the compounds in the solution system. The dried material is then calcined by heating to a temperature from about 250° C. to about 450° C., preferably 300° C. to 380° C., in air or oxygen for a period of time from about one hour to about 16 hours to produce the desired catalyst composition.

The molybdenum may be introduced into the solution in the form of ammonium salts such as ammonium paramolybdate, or organic acid salts of molybdenum such as acetates, oxalates, mandelates, and glycolates. Some other partially water soluble molybdenum compound which may also be used include molybdenum oxides, molybdic acid, and chlorides of molybdenum.

The vanadium may be introduced into the solution in the form of ammonium salts such as ammonium metavanadate and ammonium decavanadate, or organic salts of vanadium such as acetates, oxalates, and tartrates. Partially water soluble vanadium compounds such as vanadium oxides, and sulfates of vanadium can be used. To achieve a complete solubility, a certain amount of oxalic or tartaric acid can also be added.

The niobium may be used in the form of oxalates. Other sources of this metal in soluble form include compounds in which the metal is coordinated, bonded or complexed to a beta-diketonate, carboxylic acid, and amine, and alcohol, or an alkanolamine.

The phosphorus may be introduced into the solution in the form of diammonium hydrogen phosphate. Other soluble compounds of phosphorus can also be used such as phosphoric acid. Tellerium may be introduced into the solution in the form of telleuric acid or salt of tellurium. Boron may be added into the solution in the form of boric acid or salt of boron.

According to another embodiment of the invention, the catalyst is prepared by the following general procedure. The vanadium compound is mixed with water and oxalic acid to form a first solution, the niobium compound is mixed with water to form a second solution, the molybdenum compound is mixed with water to form a third solution, and phosphorus compound is mixed with water to form a fourth solution. The first and second solutions are heated separately and mixed, and then combined and heated for about fifteen minutes with continuous stirring. The third solution is heated and mixed, and then added to the combined first and second solutions to form a combined gel. The fourth solution is slowly added to the combined gel solution. After mixing and heating for about fifteen minutes, the resultant gel is dried to incipient wetness with continuous stirring at about 100° C.

After drying the resultant gel mixture at 120° C. for 16 hours, the dried material is heated to 350° C. at the rate of 2° C. per minute and calcined at this temperature in air for 4 hours to produce the desired oxide composition. This processing regime appears to be close to optimum as it allows the composition to form a catalyst with the desired structure.

The catalyst employed for practice of the process of the present invention has a structure which is poorly crystallized and can be characterized by the X-ray diffraction (XRD) pattern presented in Table 1.

TABLE 1

Catalyst XRD characteristics

| Interplanar distance (A) | Intensity (a.u.) |
|---|---|
| 4.03 | 100 |
| 3.57 | 60–85 |
| 2.01 | 40–60 |
| 1.86 | 50–70 |

To obtain this structure, the catalyst is preferably prepared as stated hereinabove. After the catalyst precursor is obtained, it is then activated by calcining. During calcining at 350° C., the partially crystallized phase specified above is formed which is believed to be the active structure in the oxidation of ethane to acetic acid. Both the amorphous phase typically obtained by calcination at temperatures lower than 350° C. and the well-crystallized structure typically obtained by calcination at temperatures higher than 350° C. are less effective with respect to production of acetic acid.

The catalyst can be promoted with one or more promoters elements without affecting the foregoing XRD pattern. We have found that the addition of small amounts of the promoter element, up to 0.1 atom per atom of vanadium, does not weaken or destroy the activity of the catalyst by changing its structure, but rather maintains the desired poor-crystallized structure. It is believed the promoter element increases the catalyst acidity. This facilitates the adsorption of ethylene as well as the desorption of acetic acid, both leading to an increase in the selectivity to acetic acid.

The present invention also relates to methods for the production of acetic acid by the catalytic oxidation of ethane with oxygen in contact with the improved catalyst.

Accordingly, yet another aspect of the invention relates to a catalytic process for preparing acetic acid by means of ethane oxidation comprising the step of oxidizing ethane in a reaction mixture comprising ethane and oxygen or a compound capable of providing oxygen in a reaction zone in the presence of a catalyst containing a catalyst composition comprising the elements Mo, V, Nb and X, in the form of oxides, in the ratio $$Mo_A V_B Nb_C X_D$$

wherein X is at least one promoter element selected from the group consisting of P, B, Hf, Te, and As;
A is a number ranging from about 1 to about 5;
B is 1;
C is a number ranging from about 0.01 to about 0.5; and
D is a number ranging from greater than 0 to about 0.1.

According to one preferred embodiment, the catalyst is in the form of a fixed or fluidized bed and the oxidation is carried out by feeding a feed mixture comprising ethane into the reaction zone. The feed mixture may further comprises air, oxygen, ethane, steam or mixtures thereof. Preferably, the feed mixture comprises 1 to 70% by volume of ethane. According to another preferred embodiment, the feed mixture comprises molecular oxygen ranging from 0.1 to 50% by volume of the feed and/or is diluted with steam in an amount ranging from 0 to 40% by volume.

According to yet another preferred embodiment, the oxidation is achieved while operating in gas phase at a temperature of from 150 to 450° C., under a pressure of from 1 to 50 bars, and/or with a contact time between the reaction mixture and catalyst of from 0.1 to 10 seconds.

The gaseous components of the reaction mixture preferably include ethane, oxygen and a diluent, and these components are uniformly admixed prior to being introduced into the reaction zone. The components may be preheated, individually or after being admixed, prior to being introduced into the reaction zone which should have temperature of from about 150° C. to about 450° C.

Another embodiment relates to a method wherein the reaction mixture used in carrying out the catalytic process generally contains one mole of ethane, 0.01 to 2.0 moles of molecular oxygen either as pure oxygen or in the form of air, and zero to 4.0 moles of water in the form of steam. The water or steam is used as a reaction diluent and as a heat moderator for the reaction. Other gases may be used as reaction diluent or heat moderators such as helium, nitrogen, and carbon dioxide.

The raw material used as the source of the ethane can be a gas stream which contains at least five volume percent of ethane. The gas stream can also contain minor amounts of the $C_3$–$C_4$ alkanes and alkenes, preferably less than five volume percent of each. The gas stream can also contain major amounts, more than five volume percent, of nitrogen, carbon dioxide, and water in the form of steam.

The reaction zone generally has a reaction pressure of from 1 to 50 bar, preferably from 1 to 30 bar. The reaction pressure is initially provided by the feed of the gaseous reactant and diluent and, after the reaction has commenced, is maintained by the use of suitable back-pressure controller placed on the reactor outlet stream. The reaction temperature is generally from about 150° C. to about 450° C., preferably from 200° C. to 300° C. The reaction temperature is provided by placing the catalyst bed within a tubular converter having walls placed in a furnace heated to the desired reaction temperature.

The reaction contact time between tie reaction mixture and the catalyst is from about 0.01 second to 100 seconds, preferably 0.1 to 50 seconds, and advantageously from 0.1 second to 10 seconds. The contact time is defined as the ratio between the apparent volume of the catalyst bed and the volume of the gaseous reaction mixture feed to the catalyst bed under the given reaction conditions in a unit of time. The reaction zone generally has a space hourly velocity of from about 50 to about 50,000 $h^{-1}$, preferably from 100 to 10,000 $h^{-1}$ and most preferably from 200 to 3,000 $h^{-1}$.

The space velocity may be calculated by determining total reactor outlet gas equivalent in liters of the total effluent evolved over a period of one hour divided by the liters of catalyst in the reactor. This room temperature volume is converted to the volume at 0° C. at 1 bar.

The oxygen concentration in the feed gas mixture can vary widely, from 0.1 to 50% or higher of the feed mixture by applying of proper measures to avoid explosion problems. Air is the preferred source of oxygen in the feed. The amount of oxygen present may be a stoichiometric amount, or higher, of the hydrocarbons in the feed.

The process is generally carried out in a single stage with all the oxygen and reactants being supplied as a single feed with unreacted initial reactants being recycled.

The process may further comprise the step of introducing oxygen into the feed mixture and/or reaction zone to increase the yield, selectivity or both yield and selectivity of acetic acid.

The oxidation performed according to the invention provides a selectivity to acetic acid of about 50% at a 50% conversion of ethane per single pass through said reaction zone.

The catalyst of the invention is not limited to use in the oxydehydrogenation of ethane to ethylene and acetic acid and may be applied, for example, in oxidizing alpha-beta unsaturated aliphatic aldehydes in the vapour phase with molecular oxygen to produce the corresponding alpha-beta unsaturated carboxylic acids.

Accordingly, the invention also relates to a process for performing a catalytic chemical reaction in fluid phase (i.e., liquid, vapor or mixtures thereof) comprising contacting at least one reactant in fluid phase under suitable reaction conditions with a catalyst containing a catalyst composition comprising the elements Mo, V, Nb and X, in the form of oxides, in the ratio $$Mo_A V_B Nb_C X_D$$

wherein X is at least one promoter element selected from the group consisting of P, B, Hf, Te, and As;
A is a number ranging from about 1 to about 5;
B is about 1;
C is a number ranging from about 0.01 to about 0.5; and
D is a number ranging from greater than 0 to about 0.1.

Another aspect relates to a process for performing a catalytic chemical reaction comprising the step of introducing a reactant in fluid phase into a reaction zone containing a catalyst having a catalyst composition comprising the elements Mo, V, Nb and X, in the form of oxides, in the ratio $$Mo_A V_B Nb_C X_D$$

wherein X is at least one promoter element selected from the group consisting of P, B, Hf, Te, and As;
A is a number ranging from about 1 to about 5;
B is 1;
C is a number ranging from about 0.01 to about 0.5; and
D is a number ranging from greater than 0 to about 0.1.

One embodiment relates to a catalytic chemical reaction which converts one or more fluid phase reactants to one or more fluid phase products. Preferably, the one or more fluid phase reactants comprise ethane and the one or more fluid phase products comprise acetic acid. More preferably, the one or more fluid phase reactants and/or one or more fluid phase products comprises one or more gaseous components.

According to another embodiment, the one or more fluid phase reactants comprise alpha-beta unsaturated aliphatic aldehydes and oxygen and the one or more fluid phase products comprise alpha-beta unsaturated carboxylic acids.

EXAMPLES

The following examples are illustrative of some of the products and methods of making the same falling within the scope of the present invention. They are, of course, not to be considered in any way limitative of the invention. Numerous changes and modification can be made with respect to the invention.

Catalytic processes using the various catalysts were carried out in a tubular reactor under the following conditions. Gas feed composition was 15% by volume ethane and 85% by volume air. All experiments were run at a temperature of 260° C., a pressure of 200 psig and a space velocity of about 1,100 $h^{-1}$. The reactor consisted of a 6 millimeter diameter stainless steel straight tube heated in an oven. The reactor contained 3.0 grams of the catalyst. The reactor bed depth was about 6.0 centimeters so that the depth to cross-section ratio was about ten. Reaction products were analyzed on-line by gas chromatography. Oxygen, nitrogen and carbon monoxide were analyzed using a 3 mm by 3 mm column of 13X molecular sieve. Carbon dioxide, ethane and ethylene and water were analyzed using a 1.8 m by 3 mm column packed with material sold under the tradename HAYASEP™ Q. Acetic acid was were analyzed using a 0.5 m by 3 mm column packed with material sold under the trademark PORAPACK™ N.

In all cases, the conversion and selectivity calculations were based on the stoichiometry:

$C_2H_6 + 0.5\ O_2 \rightarrow C_2H_4 + H_2O$ $C_2H_6 + 1.5\ O_2 \rightarrow C_2H_4O_2 + H_2O$ $C_2H_6 + 2.5\ O_2 \rightarrow 2\ CO + 3\ H_2O$ $C_2H_6 + 3.5\ O_2 \rightarrow 2\ CO_2 + 3\ H_2O$ The yield of acetic acid was calculated by multiplying the selectivity to acetic acid by ethane conversion.

EXAMPLE 1

A catalyst was prepared to have the following composition:

$Mo_{2.5}V_{1.0}Nb_{0.32}$

Ammonium metavanadate in the amount of 11.4 grams was added to 120 ml of distilled water and heated to 90° C. with stirring. 2.5 grams of oxalic acid were added. to obtain a clear yellow colour solution with a pH between 5 and 6 (Solution A). 19.4 grams of niobium oxalate containing 21.5% by weight calculated as $Nb_2O_5$ were added to 86 ml of water and heated to 65° C. with continuous stirring to obtain a clear white colour solution with a pH of 1 (Solution B). Solution B was then combined with Solution A. The combination was heated at 90° C. and 28 grams of oxalic acid were added very slowly with continuous stirring to give Solution C. Ammonium paramolybdate in the amount of 43.2 grams was added to 45 ml of water and heated to 60° C. to give a colourless solution with a pH between 6.0 and 6.5 (Solution D). Solution D was combined slowly with Solution C to give dark blue to dark gray colour precipitates (Mixture E). This dark colour combination was stirred vigorously to achieve a homogeneous gel mixture which was then dried slowly to incipient dryness within 60 to 120 minutes at 95–98° C. with continuous stirring.

The resulting solid was put in a China dish and dried further in an oven at 120° C. for sixteen hours. The dried material was cooled to room temperature and placed in a furnace. The temperature was raised from room temperature to 350° C. at the rate of 2°/min and thereafter held at 350° C. for four hours.

Calcined catalyst was formulated into uniform particles of the 40–60 mesh size and tested according to the described test. The results are shown in Table 3.

EXAMPLES 2 TO 9

Using the procedure of Example 1, phosphorus containing catalysts of the following general formula were prepared:

$Mo_{2.5}V_{1.0}Nb_{0.32}P_x$ where X is 0.01 to 1.0.

The required amount of diammonium hydrogen phosphate was added to about 5 to 10 ml of distilled water and combined slowly with the gel mixture formed from mixing ammonium metavanadate, niobium oxalate and ammonium paramolybdate solutions (Mixture E in Example 1). After achieving a homogeneous mixture, the resultant gel was dried slowly to incipient dryness at 95–98° C. with continuous stirring. The drying and calcination procedures were the same as used in Example 1. Table 2 shows weight of the phosphorus salt added to the base case catalyst, grams of phosphorus salt per gram of catalyst and catalyst composition.

EXAMPLE 10

Using the procedure of Example 1, tellurium containing catalyst was prepared by adding of 3.81E-o4 g of telleuric acid to the gel mixture E in Example 1. Drying and calcination of the catalyst was done by following the procedure mentioned in Example 1.

EXAMPLE 11

Using the procedure of Example 1, boron containing catalyst was prepared by adding of 1.344E-o3 g of boric acid to the gel mixture E in Example 1. Drying and calcination of the catalyst was done by following the procedure mentioned in Example 1.

TABLE 2

Phosphorus containing catalysts

| Example | $(NH_4)_2HPO_4$ (g) | g of phos./g of catalyst | Catalyst composition |
|---|---|---|---|
| 2 | 0.133 | 0.00289 | $Mo_{2.5}V_{1.0}Nb_{0.32}P_{0.01}$ |
| 3 | 0.166 | 0.00360 | $Mo_{2.5}V_{1.0}Nb_{0.32}P_{0.013}$ |
| 4 | 0.333 | 0.00867 | $Mo_{2.5}V_{1.0}Nb_{0.32}P_{0.03}$ |
| 5 | 0.534 | 0.01160 | $Mo_{2.5}V_{1.0}Nb_{0.32}P_{0.042}$ |
| 6 | 0.800 | 0.01730 | $Mo_{2.5}V_{1.0}Nb_{0.32}P_{0.06}$ |
| 7 | 1.190 | 0.02500 | $Mo_{2.5}V_{1.0}Nb_{0.32}P_{0.1}$ |
| 8 | 2.080 | 0.04500 | $Mo_{2.5}V_{1.0}Nb_{0.32}P_{0.2}$ |
| 9 | 10.04 | 0.21800 | $Mo_{2.5}V_{1.0}Nb_{0.32}P_{1.0}$ |
| 10 | $3.81 \times 10^{-4}$ | $2.12 \times 10^{-4}$ | $Mo_{2.5}V_{1.0}Nb_{0.32}Te_{1.69E-05}$ |
| 11 | $1.35 \times 10^{-3}$ | $2.36 \times 10^{-4}$ | $Mo_{2.5}V_{1.0}Nb_{0.32}B_{2.23E-05}$ |

The results of the tests with these catalysts under the reaction conditions described above are given in Table 3.

TABLE 3

Results of testing catalyst activity and selectivity

| Example | Conversion (%) | S. Conv.** (%/m$^2$) | Selectivity (%) AA* | Selectivity (%) $C_2H_4$ | AA yield (%) | BET surf. area (m$^2$/g) |
|---|---|---|---|---|---|---|
| 1 | 65.0 | 0.85 | 30.5 | 26.9 | 19.8 | 25.6 |
| 2 | 60.0 | 1.04 | 38.5 | 24.1 | 23.1 | 19.3 |
| 3 | 63.2 | 1.11 | 33.8 | 25.3 | 21.3 | 18.9 |
| 4 | 62.2 | 1.21 | 36.6 | 24.1 | 22.8 | 17.1 |
| 5 | 53.3 | 0.99 | 49.9 | 10.5 | 26.6 | 17.9 |
| 6 | 33.6 | 1.29 | 50.2 | 14.7 | 16.9 | 8.7 |
| 7 | 52.8 | 1.20 | 23.3 | 43.6 | 12.3 | 14.7 |
| 8 | 20.1 | 1.28 | 11.7 | 58.7 | 2.4 | 5.2 |
| 9 | 0 | — | 0 | 0 | 0 | 0.5 |
| 10 | 62.86 | 0.84 | 37.2 | 28.40 | 23.35 | 25 |
| 11 | 64.41 | 0.93 | 38.2 | 26.32 | 24.61 | 23 |

*AA denotes acetic acid
**S.Conv is Specific conversion of ethane per unit area = Conversion/specific surface area (%/m2)

As shown in Table 3, when increasing the amount of phosphorus introduced into the MoVNb oxide catalyst, ethane conversion and selectivities to mild oxidation products change as follows:

conversion tends to decrease, total selectivity to ethylene and acetic acid somewhat increases, selectivity to ethylene goes through a minimum, selectivity to acetic acid passes through a maximum.

Since the activities of all samples were measured using the same amount of catalyst (3 g), the differences in ethane conversion might be caused by different specific surface areas of catalysts. Indeed, catalytic activity expressed as the conversion per surface area, as is seen from Table 3, does not change strongly with the amount of phosphorus in the catalyst. This means that small amounts of phosphorus ranging from 0 to 0.2 atom per atom of vanadium do not alter practically the specific overall activity of the MoVNb oxide catalyst in the oxidation of ethane.

Figure 2:
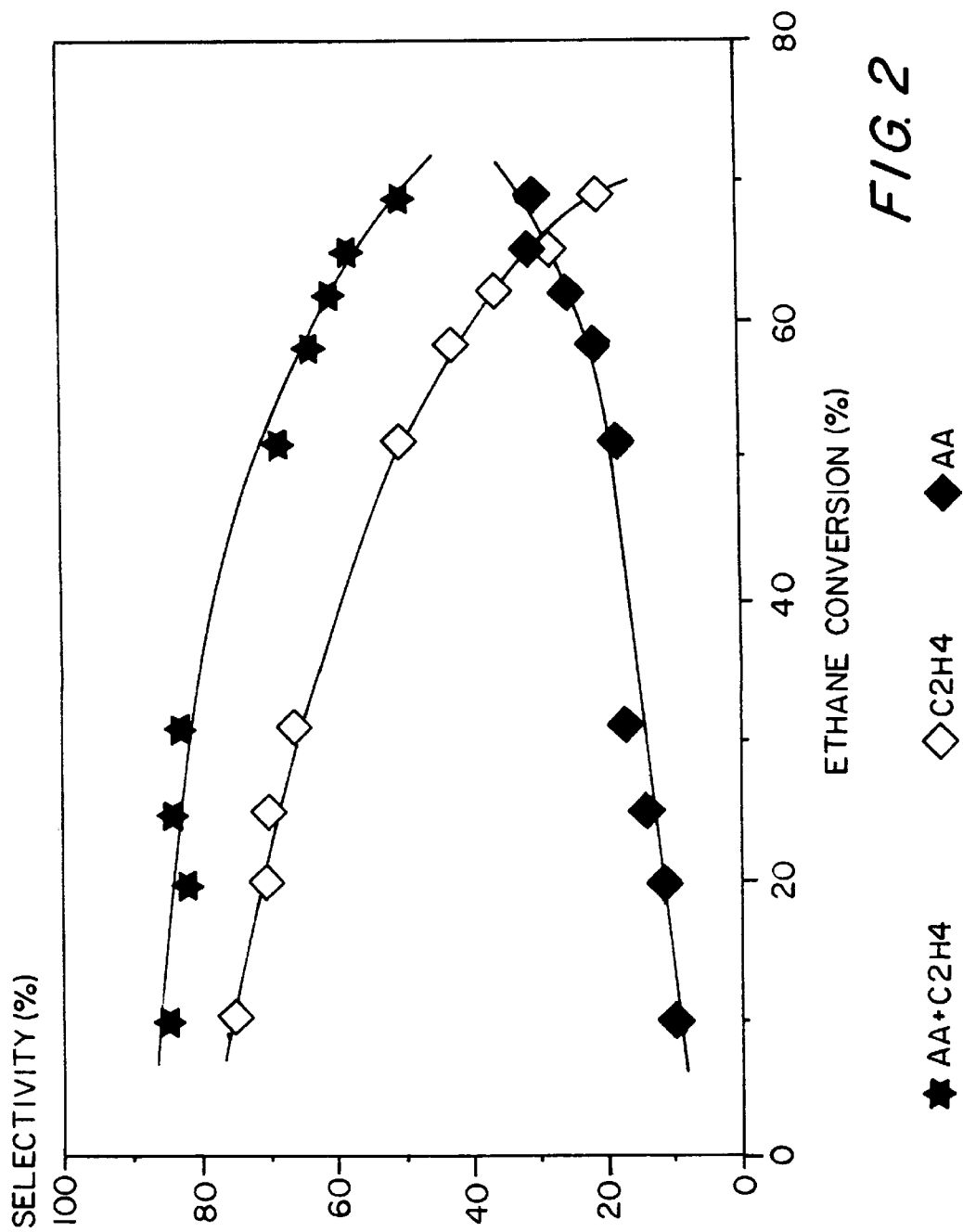
FIG. 2 is a graphical representation of the relationship between selectivity (%) and ethane conversion (%) showing selectivity plots for acetic acid (AA), ethylen/e ($C_2H_4$), and acetic acid and ethylene (AA+$C_2H_4$), wherein the vertical axis represents selectivity (%) and horizontal axis represents ethane conversion (%).

Generally, total selectivity to ethylene and acetic acid decreases with the conversion of ethane. FIG. 2 shows a typical curve relating selectivity to ethylene plus acetic acid to conversion of ethane for the unmodified MoVNb oxide catalyst over the preferred operating regime. From this figure, it can be seen also that the selectivity to ethylene declines while the selectivity to acetic acid increases with increasing ethane conversion. Taking into account these dependencies, a slight increase of the total selectivity to ethylene and acetic acid with the amount of phosphorus in the catalyst can be related to the decrease of ethane conversion observed on F-doped catalysts.

This explanation is not valid for the single selectivities to ethylene and acetic acid which changed non-monotonically with the concentration of phosphorus in the catalyst. It is believed that small amounts of phosphorus, between 0.01 and 0.1 atom per atom of vanadium, mainly increase catalyst surface acidity to the extent which is substantial for the consecutive oxidation of ethylene to acetic acid. As a result, the specific catalytic activity does not change considerably, but the selectivity to acetic acid increases. Similar effects of an increase in acetic acid selectivity or yield by addition of Te and B as a promoter to MoVNb catalytic system is achieved, Table 3.

The above description of the invention is intended to be illustrative and not limiting. Various changes or modifications in the embodiments described may occur to those skilled in the art. These can be made without departing from the spirit or scope of the invention.

It is claimed:

1. A catalyst for selective oxidation of ethane to acetic acid containing a catalyst composition consisting essentially of the elements Mo, V, Nb and X, in the form of oxides, in the following ratio:

$$Mo_A V_B Nb_C X_D$$

wherein X is P;
A is about 2.5;
B is 1;
C is about 0.3; and
D is a number ranging from greater than about 0.01 to about 0.1.

2. A catalyst for selective oxidation of ethane to acetic acid containing a catalyst composition consisting essentially of the elements Mo, V, Nb and X and oxygen in the following ratio:

$$Mo_A V_B Nb_C X_D O_Y$$

wherein X is P;
A is about 2.5;
B is 1;
C is about 0.3;

D is a number ranging from greater than about 0.01 to about 0.1; and
Y is a number determined by the valence requirements of the other elements in the catalyst composition.

3. A catalyst for selective oxidation of ethane to acetic acid made by process comprising the steps of:
    (a) combining the elements Mo, V, Nb and X in the following ratio:

$$Mo_A V_B Nb_C X_D$$

to form a mixture,
    wherein X is P;
    A is about 2.5;
    B is about 1;
    C is about 0.3; and
    D is a number ranging from greater than about 0.01 to about 0.1; and
    (b) calcining said mixture to form said catalyst.

4. The catalyst of claim 1, wherein D is about 0.03 to about 0.05.

5. The catalyst of claim 2, wherein D is about 0.03 to about 0.05.

6. The catalyst of claim 1, wherein D is about 0.04.

7. The catalyst of claim 2, wherein D is about 0.04.

8. The catalyst of claim 1, wherein said catalyst is a supported catalyst comprising a support.

9. The catalyst of claim 8, wherein said support is selected from the group consisting of alumina, silica, titania, zirconia, zeolites and molecular sieves.

10. The catalyst of claim 8, wherein said support comprises a microporous material, nanoporous material or mixtures thereof.

11. The catalyst of claim 8, wherein said supported catalyst comprises from 10 to 50% by weight catalyst composition and 90 to 50% by weight support.

12. A process of forming the catalyst of claim 1, comprising the steps of:
    (a) forming a mixture consisting essentially of Mo, V, Nb and X in a solution;
    (b) drying said mixture to form a dried solid material; and
    (c) calcining said dried solid material to form said catalyst.

13. The process of claim 12, wherein said mixture is an aqueous system having a pH from 1 to 10.

14. The process of claim 12, wherein said mixture is an aqueous system having a pH from 1 to 7.

15. The process of claim 12, wherein said mixture is formed by combining a first solution with a second solution, wherein said first solution and said second solution each contain at least one element selected from the group consisting of Mo, V, Nb and X.

16. The process of claim 12, wherein said calcining comprises heating said dried solid material to a calcining temperature from about 250° C. to about 450° C. in air or oxygen for a period of time ranging from about one hour to about 16 hours.

17. The process of claim 12, wherein said mixture further comprises a support.

18. The process of claim 17, wherein said support is selected from the group consisting of alumina, silica, titania, zirconia, zeolites and molecular sieves.

19. The catalyst of claim 2, wherein said catalyst is a supported catalyst comprising a support.

20. The catalyst of claim 19, wherein said support is selected from the group consisting of alumina, silica, titania, zirconia, zeolites and molecular sieves.

21. The catalyst of claim 3, wherein said catalyst is a supported catalyst comprising a support.

22. The catalyst of claim 3, wherein D is about 0.03 to about 0.05.

23. The catalyst of claim 22, wherein said catalyst is a supported catalyst comprising a support.

24. The catalyst of claim 23, wherein said support is selected from the group consisting of alumina, silica, titania, zirconia, zeolites and molecular sieves.

25. The catalyst of claim 23, wherein said support comprises a microporous material, nanoporous material or mixtures thereof.

26. The catalyst of claim 23, wherein said supported catalyst comprises from 10 to 50% by weight catalyst composition and 90 to 50% by weight support.

27. A process of forming the catalyst of claim 2, comprising the steps of:
   (a) forming a mixture consisting essentially of Mo, V, Nb and X in a solution;
   (b) drying said mixture to form a dried solid material; and
   (c) calcining said dried solid material to form said catalyst.

28. The process of claim 27, wherein said mixture is an aqueous system having a pH from 1 to 10.

29. The process of claim 27, wherein said mixture is an aqueous system having a pH from 1 to 7.

30. The process of claim 27, wherein said mixture is formed by combining a first solution with a second solution, wherein said first solution and said second solution each contain at least one element selected from the group consisting of Mo, V, Nb and X.

31. The process of claim 27, wherein said calcining comprises heating said dried solid material to a calcining temperature from about 250° C. to about 450° C. in air or oxygen for a period of time ranging from about one hour to about 16 hours.

32. The catalyst of claim 3, wherein said catalyst is a supported catalyst comprising a support.

33. The catalyst of claim 32, where said support is selected from the group consisting of alumina, silica, titania, zirconia, zeolites and molecular sieves.

34. The catalyst of claim 32, wherein said support comprises a microporous material, nanoporous material or mixtures thereof.

35. The catalyst of claim 32, wherein said supported catalyst comprises from 10 to 50% by weight catalyst composition and 90 to 50% by weight support.

* * * * *